US00PP32118P2

(12) United States Plant Patent
Korlipara

(10) Patent No.: US PP32,118 P2
(45) Date of Patent: Aug. 25, 2020

(54) ***VERONICA* PLANT NAMED 'TNVEOVB'**

(50) Latin Name: ***Veronica* hybrid**
Varietal Denomination: TNVEOVB

(71) Applicant: Terra Nova Nurseries, Inc., Canby, OR (US)

(72) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 16/602,227

(22) Filed: Aug. 29, 2019

(51) Int. Cl.
*A01H 5/02* (2018.01)
*A01H 6/68* (2018.01)

(52) U.S. Cl.
USPC ..... Plt./251
CPC ..... *A01H 6/68* (2018.05)

(58) Field of Classification Search
USPC ..... Plt./251
CPC ..... A01H 6/68
See application file for complete search history.

*Primary Examiner* — Anne Marie Grunberg
(74) *Attorney, Agent, or Firm* — Klarquist Sparkman, LLP

(57) ABSTRACT

A new and distinct form of *Veronica* plant characterized by dark, saturated purple-blue flowers, a compact, slow spreading, low mounding habit, excellent dense branching with flower spikes at the end of every branch, medium green leaves, good garden performance, and excellent vigor.

1 Drawing Sheet

Botanical Denomination: *Veronica* hybrid.
Variety Designation: 'TNVEOVB'.
Trade Designation: VESPERS™ Blue.

BACKGROUND OF THE INVENTION

The present invention relates to a new and distinct cultivar of *Veronica* given the name of 'TNVEOVB'. *Veronica* is in the family Plantaginaceae (formerly Scrophulariaceae). This plant was part of a controlled breeding program to produce a compact, medium short plant with long lasting flower spikes of dark, saturated purple-blue. The exact parents of this selection are unknown, unnamed, proprietary interspecific hybrids bred from *Veronica longifolia* and *Veronica spicata*. This plant was selected for its similarity in habit, bloom time, and overall look to *Veronica* 'TNVERA' and will be sold as a series.

Compared to *Veronica* 'TNVERA', U.S. Plant Pat. No. 26,416, the new cultivar has purple-blue flowers rather than pink.

Compared to *Veronica spicata* 'Ulster Blue Dwarf', an unpatented plant, the new cultivar has a more compact habit and is cone shaped when in flower rather than flat on top.

The new cultivar exhibits the following characteristics:

1. dark, saturated purple-blue flowers,
2. a compact, slow spreading, low mounding habit,
3. excellent dense branching with flower spikes at end of every branch,
4. medium green leaves,
5. good garden performance, and
6. excellent vigor.

The new variety has been reproduced only by asexual propagation (stem cuttings and micropropagation). Each of the progeny exhibits identical characteristics to the original plant. Asexual propagation by division and micropropagation as done in Canby, Oreg. shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a one-year-old *Veronica* 'TNVEOVB' growing in the trial field in early June in Canby, Oreg.

FIG. 2 shows multiple one-year-old *Veronica* 'TNVEOVB' growing in the trial field in June in Canby, Oreg.

DETAILED DESCRIPTION

The following is a detailed description of the new *Veronica* cultivar based on observations of two-year-old specimens growing in the trial beds in full sun in June in Canby, Oreg. Canby is in Zone 8 on the USDA Hardiness map. Temperatures range from a high of 95 degrees F. in August to an average of 32 degrees F. in January. Normal rainfall in Canby is 42.8 inches per year. The color descriptions are all based on The Royal Horticultural Society Colour Chart, 5$^{th}$ edition, 2007, except where general color terms of ordinary dictionary significance are used.

Plant:

*Form.*—Mounding.
*Type.*—Evergreen, mounding subshrub.
*Cold hardiness.*—USDA Zones 4-8.
*Size.*—Grows to 35 cm wide and 28 cm tall from soil to top of the flowers.
*Vigor.*—Excellent.
*Branching.*—Extremely well branched with about 100 stems from the crown, older stems branching freely.

*Stem.*—Grows up to 16 cm long, pubescent, internodes range from 0.5 to 2 cm long, young stems Yellow Green 147C; older woody stems grow to 6 mm wide, Brown 200A.

*Stem strength.*—Very strong.

*Roots.*—Fibrous, freely branching, plants root easily from stem tip cuttings.

Leaf:

*Type.*—Simple.

*Arrangement.*—Opposite.

*Blade size.*—Grow to 3 cm long and 1 cm wide.

*Leaf number.*—1500.

*Petiole description.*—Sessile.

*Shape.*—Lanceolate.

*Venation.*—Pinnate.

*Margins.*—Serrate.

*Apex.*—Acute.

*Base.*—Attenuate.

*Surface texture.*—Pubescent of both sides.

*Leaf rugosity.*—Absent.

*Leaf color.*—Top side Green N137A with main vein 147B, bottom side Green 137B with main vein 147B.

Inflorescence:

*Type.*—Terminal raceme.

*Number of flowers.*—About 140 per raceme.

*Size of inflorescence.*—Spreads 2.5 cm wide and 12 cm long.

*Peduncle.*—15 to 20 mm long and 2 mm wide, pubescent, Yellow Green 147B.

*Pedicel.*—1 mm long and 1 mm wide, pubescent, Yellow Green 147B.

*Bloom period.*—Middle of May to end of June with some rebloom in August in Canby, Oreg.

Flower bud:

*Size.*—6 mm long and 2 mm wide at the widest point prior to opening.

*Description.*—Convolute, narrowly oblong, apex obtuse.

*Surface texture.*—Glabrous.

*Color.*—Between Violet Blue N89C and Violet Blue N89D.

Flower:

*Type.*—Regular.

*Shape.*—Rotate.

*Corolla description.*—5 mm wide and 7 mm deep; both sides glabrous, tube 3 mm long and 1.5 to 2.5 mm wide, between Violet Blue N89C and Violet Blue N89D, 4 lobes, between Violet Blue N89C and Violet Blue N89D, upper lobe broadly obovate, 3 mm long and 4 mm wide, tip obtuse, margin erose, side and bottom lobes 5 mm long and 3 mm wide, obovate, tip obtuse, margin entire.

*Calyx description.*—Campanulate, 2 mm wide and 3 mm deep, 4-lobed, lobes ovate, tips acute, margins entire, Green 137A and pubescent on both sides.

*Pistil description.*—1, 8 mm long, ovary round, 1 mm long and 1 mm wide, Yellow Green 144A, style 7 mm long, Violet Purple N89A, stigma Violet Purple N89A.

*Stamen description.*—2, filaments 8 mm long and Violet Purple N89A, anthers 1.5 mm long and Violet Purple N89A, pollen White NN155C.

*Pollen amount.*—Low.

*Flower density.*—High.

*Fragrance.*—None.

*Lastingness.*—A raceme blooms for about 2 weeks on the plant.

Seed: None.

Pests and diseases: Disease and pest resistance is beyond what is typical for *Veronica* species.

I claim:

1. A new and distinct form of *Veronica* plant substantially as shown and described.

* * * * *

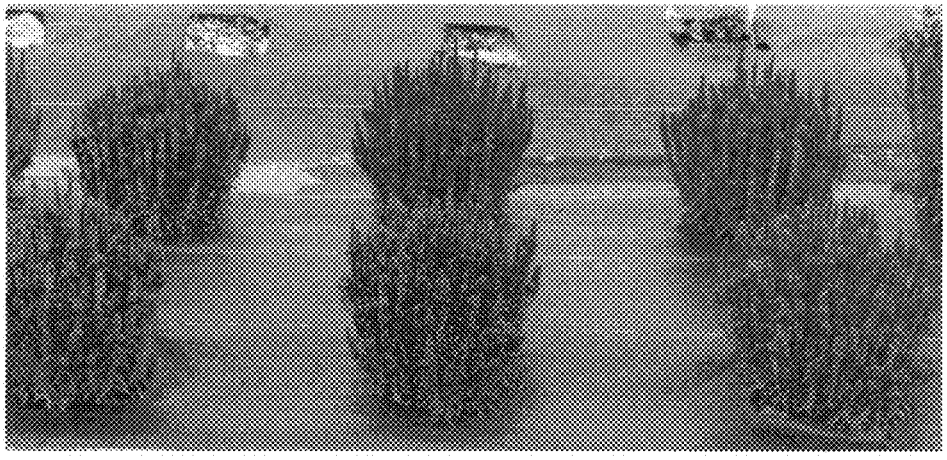

Fig. 1 Below
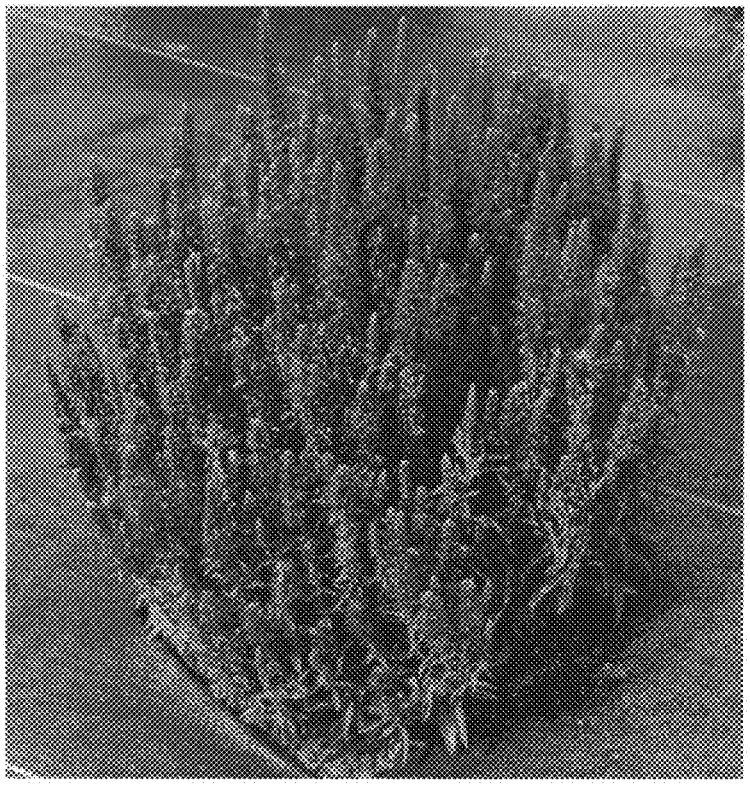
Fig. 2 Below